(12) United States Patent
Rebhan

(10) Patent No.: US 6,587,202 B2
(45) Date of Patent: Jul. 1, 2003

(54) OPTICAL MATERIALS TESTING METHOD

(75) Inventor: Ulrich Rebhan, Goettingen (DE)

(73) Assignee: Lambda Physik AG, Goettingen (DE)

( * ) Notice: Subject to any disclaimer, the term of this patent is extended or adjusted under 35 U.S.C. 154(b) by 312 days.

(21) Appl. No.: 09/726,871

(22) Filed: Nov. 30, 2000

(65) Prior Publication Data

US 2001/0043331 A1 Nov. 22, 2001

Related U.S. Application Data

(60) Provisional application No. 60/178,804, filed on Jan. 28, 2000.

(51) Int. Cl.[7] .............................................. G01N 21/00
(52) U.S. Cl. .......................... 356/432; 356/124; 374/32; 374/45
(58) Field of Search ................................ 356/432, 433, 356/434, 435, 436, 437, 440, 128, 517, 237.1, 239.1, 239.2, 124; 374/32, 45; 250/330, 341.6

(56) References Cited

U.S. PATENT DOCUMENTS

| | | | |
|---|---|---|---|
| 3,654,626 A | | 4/1972 | Geller et al. .......... 340/173 CC |
| 3,723,007 A | | 3/1973 | Leonard ...................... 356/75 |
| 4,091,681 A | * | 5/1978 | Hordvik ...................... 73/574 |
| 4,182,574 A | | 1/1980 | Quillfeldt .................... 356/318 |
| 4,362,364 A | | 12/1982 | Smith .......................... 350/358 |
| 4,381,148 A | * | 4/1983 | Ulrich et al. ............... 356/213 |
| 4,429,999 A | * | 2/1984 | Bimberg et al. ............. 356/432 |
| 4,447,153 A | | 5/1984 | Cremers et al. ............. 356/361 |
| 4,799,767 A | | 1/1989 | Woodruff .................... 350/269 |
| 4,868,768 A | | 9/1989 | Draggoo et al. ............ 364/525 |
| 5,015,096 A | * | 5/1991 | Kowalski et al. ........... 356/613 |
| 5,696,580 A | * | 12/1997 | Kubo et al. ................. 356/72 |
| 5,894,352 A | | 4/1999 | Morton ....................... 356/432 |
| 6,317,203 B1 | * | 11/2001 | Wakabayashi et al. ... 356/237.1 |
| 6,515,741 B1 | * | 2/2003 | Basting et al. ........... 356/237.1 |

OTHER PUBLICATIONS

Itoh, et al., "Absorption Measurement of the Optical Materials by Real Time Holographic Interferometry," *Optics Communications*, vol. 33, No. 2, May 1980, pp. 183–187.

Leclerc, et al., "Transient Absorption and Fluorescence Spectroscopy in Fused Silica Induced by Pulsed KrF Excimer Laser Irradiation," *Appl. Phys. Lett.*, vol. 59, No. 23, Dec. 1991, pp. 3369–3371.

Sahba, et al., "Infrared Absorption Coefficients of Silica Glasses," *Journal of the American Ceramic Society*, vol. 75, No. 1, Jan. 1992, pp. 209–212.

Schenker, et al., "Ultraviolet Damage Properties of Various Fused Silica Materials," *SPIE*, vol. 2428, Sep. 1995, pp. 458–468.

(List continued on next page.)

*Primary Examiner*—Hoa Q. Pham
(74) *Attorney, Agent, or Firm*—Stallman & Pollock LLP

(57) ABSTRACT

A method for testing a material block prior to forming the material block into one or more optical components for use with a sub-micron lithographic, high power, narrow bandwidth laser system having high wavelength stability includes the step of selecting a block of material having appropriate characteristic optical properties for the source laser system being used. The next step is to test the material block for absorption performance. Then, if the block exhibits a sufficient absorption performance, then one of more optical components such as one or more prisms, etalons, and/or windows, etc. are formed from the material block. Finally, the optical components formed from the block are inserted into a wavelength selection module of the resonator of the laser to participate in producing a high power, narrow bandwidth laser beam which may be used in sub-micron photolithographic applications.

17 Claims, 2 Drawing Sheets

OTHER PUBLICATIONS

Drexlin, et al., "Spectral Attenutation Length of Scintillating Fibers," *Nuclear Instruments and Methods in Physics Research*, vol. 360, Nos. 1, 2, 1995, pp. 245–247.

Malo, et al., "Enhanced Photosensitivity in Lightly Doped Standard Telecommunication Fibre Exposed to High Fluence ArF Excimer Laser Light," *Electronics Letters*, vol. 31, No. 11, May 25, 1995, pp. 879–880.

*Laser–Induced Damage in Optical Materials: 1994, SPIE*, vol. 2428.

Klein, P.H., et al., "Potassium Bromide for Infrared Laser Windows: Crystal Growth, Chemical Polishing, and Optical Absorption," *Infrared Laser Windows*, vol. 11, No. 10, 1976, pp. 1335–1342.

Glass, A.J., et al., "Laser Induced Damage in Optical Materials," *National Bureau of Standards, presented at the Annual Symposium on Optical Materials for High Power Lasers*, Sep. 1978, 328 pages.

Edwards, D.F., "Low–level Losses in Ultraviolet Laser Window Materials," *SPIE PRoceedings of the Loas Almos Conference on Optics '81*, vol. 288, 1981, pp. 18–20.

Swimm, et al., "Calorimetric Study of Optical Absorption of Suprasil W–1 Fused Quartz," *NITIS*, Sep. 1984,8 pages.

Laidler, et al., "The Effect of Impurities on U.V. Damage in CaF2," *NIST Special Publication 752, 18 Symposium on Optical Materials fir High Power Lasers*, 1988, pp. 151–158.

Brimacombe, et al., "Limitations of Fiber–optic Transmission at Short Excimer Laser Wavelengths," *Conference on Lasers and Electro–Optics, 1988 Technical Digest Series*, vol. 7, 1988.

Partlo, W.N., et al., "Characterization Methods for Excimer Exposure of Deep–UV Pellicles," *SPIE Optical/Laser Microlithography III*, vol. 1264, 1990, pp. 564–575.

Ihlemann, J., et al., "Nanosecond and Femtosecond Excimer Laser Ablation of Fused Silica," *Applied Physics A*, vol. 54, No. 4, 1992, pp. 363–368.

Bagratashvili, V. N., et al., "Inhomogenous Nature of UV Absorption Bands of Bulk and Surface Oxygen–Deficient Centers in Silica Glasses," *Journal of Non–Crystalline Solids*, vol. 180, 1995, pp. 221–229.

Whitman, P.K., et al., "Laser–induced Damage of Absorbing and Diffusing Glass Surfaces under IR and UV Irradiation," *Proceedings of the 1998 $30^{th}$ Annual Boulder Damage Symposium on Optical Materials for High Power*, vol. 3578, 1999, pp. 681–391.

* cited by examiner

OPTICAL MATERIALS TESTING METHOD

PRIORITY

This application claims the benefit of priority to United States provisional patent application no. 60/178,804, filed Jan. 28, 2000.

BACKGROUND OF THE INVENTION

1. Field of the Invention

The invention relates to optical materials testing, and particularly for optical materials of components such as prisms, windows or etalons of a resonator arrangement of a gas discharge laser system such as an excimer or molecular fluorine laser.

2. Discussion of the Related Art

Integrated circuit device technology has entered the sub 0.25 micron regime, thus necessitating very fine photolithographic techniques. The reduction in size of a structure produced on a silicon wafer is limited by the ability to optically resolve the structure. This resolution ability depends directly upon the photolithographical source radiation and optics used.

Excimer lasers emitting pulsed UV-radiation are becoming increasingly important instruments in specialized material processing. The term "excimer" was first utilized as an abbreviation for "excited dimer", meaning two or more identical atoms comprising a molecule which only exists in an excited state, such as $Ar_2$ and $Xe_2$. Today, the term "excimer" has a broader meaning in the laser world and encompasses such rare gas halides as XeCl (308 nm), KrF (248 nm), ArF (193 nm), KrCl (222 nm), and XeF (351 nm). Additionally, $F_2$ (157 nm) may be used as an active media within excimer laser discharge chambers. The molecular fluorine ($F_2$) laser is in fact typically referred to as an excimer laser, and thus when the term excimer laser is used in this application, it is intended that the molecular fluorine laser be included within the meaning of that term.

As is apparent, many excimer lasers radiate at ultraviolet wavelengths making them desirable for use as lithography tools. The KrF-excimer laser emitting around 248 nm and the ArF-excimer laser emitting around 193 nm are rapidly becoming the light sources of choice for photolithographic processing of integrated circuit devices (IC's). The $F_2$-laser is also being developed for such usage and emits light around 157 nm.

To produce smaller feature sizes on IC chips, stepper and scanner machines are using expensive large scale submicron projection objectives for imaging a reticle onto a wafer surface with high diffracting-limited precision. The objectives operate at deep ultraviolet (DUV) wavelengths, such as the emission wavelengths of excimer lasers. For example, the KrF-excimer laser emitting around 248 nm is currently being used as a DUV radiation source. To reach greater resolution limits, the large field objective lenses are designed and optimized in view of various possible and discovered imaging errors. The design optimization of the objectives is, however, inadequate to meet the precision demands of sub-quarter micron lithographic technology.

One way to improve the resolvability of structures on IC chips is to use more nearly monochromatic source radiation, i.e., radiation having a reduced bandwidth, $\Delta\lambda$. Other strategies include using shorter absolute wavelength, $\lambda$, radiation such as that emitted around 193 nm and 157 nm by ArF- and $F_2$-lasers, respectively, and increasing the numerical aperture (NA) of the projection optics.

The smallest structure resolvable on an IC chip depends on the "critical dimension" (CD) of the photolithography equipment being used:

$$CD = K_1 \cdot \lambda / NA \qquad (1),$$

where NA is the numerical aperture and is a measure of the acceptance angle of the projection optics, $\lambda$ is the wavelength of the source radiation, and $K_1$ is a constant around approximately 0.6–0.8.

Simply increasing the numerical aperture NA to reduce the critical dimension CD according to (1), however, simultaneously reduces the depth of focus DOF of the projection lens by the second power of NA:

$$DOF = K_2 \cdot \lambda / (NA)^2 \qquad (2),$$

where $K_2$ is a constant around approximately 0.8–1.0. Reducing the DOF complicates wafer adjustment and adds further demand for improved chromatic correction of the projection lenses. Additionally, increasing the numerical aperture NA to reduce the critical dimension CD for achieving smaller structures requires a decrease in the bandwidth $\Delta\lambda$ of laser emission according to:

$$\Delta\lambda = K_3 \cdot \lambda / (NA)^2 \qquad (3),$$

where $K_3$ is a constant dependent on parameters associated with the projection optics. Each of the above, i.e., (1), (2) and (3), assumes that such other laser parameters as repetition rate, stability, and output power remain constant.

To produce smaller features on silicon substrates, the projection optics may be modified to increase the numerical aperture of the system or the bandwidth of the exposure radiation may be reduced, as discussed. For the reasons provided above, it is most advantageous to use a shorter wavelength exposure radiation source to facilitate smaller feature size production, in combination with narrowing the bandwidth and using projection optics of appropriate numerical aperture.

Another significant feature of a desired narrow band laser to be used advantageously for resolving small features on chips is that the laser system also exhibits high absolute wavelength stability. For example, a laser output beam wavelength stability around or below 0.1 pm is desired.

It is also desired to operate the laser at a high repetition rate. For example, it is desired to have a laser operating above 1 kHz, and particularly around 2 kHz, or more. At higher operating power, though, the amount of induced absorption at transmissive optical component in the laser resonator correspondingly increases.

Increased absorption leads to undesirable reduced wavelength stability since the temperatures of the optical components within the resonator influence the range of wavelengths that fall within the acceptance angle of the resonator. For example, the refractive index of a prism depends on its temperature and influences its wavelength dependent refractive properties. Absorption in etalon plates can affect the effective etalon finesse and can increase the laser radiation bandwidth. A window, plate or other transmissive or reflective component in the resonator can undergo surface distortions as its temperature fluctuates that can result in a degradation of many significant beam parameters. The effect is pronounced for laser systems operating in burst mode, since the components absorb significantly during a burst and heat up, and then cool down during pauses between bursts.

It is desired, then, to minimize the amount of absorption of optical components in the laser resonator. One way is to test the components in advance of placing them in the laser resonator to ensure their absorption constants are sufficiently low. U.S. Pat. No. 5,894,352 to Morton, which is hereby incorporated by reference into the present application, discloses an apparatus and method for performing such testing of prisms. Morton's technique arranges several prisms in series each having a temperature sensor in its vicinity for measuring its temperature. Then, a beam is passed through the prisms and the temperatures measured with the sensors. Those prisms that perform poorly such as by exhibiting an undesirably high rate of increase in temperature due to absorption are advantageously sorted out from satisfactory prisms before they are used in a laser system.

RECOGNIZED IN THE PRESENT INVENTION

It is recognized in the present invention that a drawback of conventional techniques is that significant time and cost of manufacturing the prisms or other optical components that are ultimately thrown out as a result of the test is wasted. It is also recognized in the present invention that the material block from which prisms, etalon plates and other optics are formed generally exhibits either a high or low absorption performance before the optics are even manufactured from the material block. It is desired to preserve the time and cost that are wasted in conventional testing techniques that manufacture optical components, such as may be subject to precise specifications, only to determine later on that the material exhibits unsatisfactory absorption performance. It is also desired to have a narrow band laser system for photolithographic production of fine structures that operates at a high repetition rate and exhibits satisfactory wavelength stability partly because the optical components of the system do exhibit satisfactory absorption performance.

SUMMARY OF THE INVENTION

It is an object of the invention to provide a high repetition rate (e.g., 1–2 kHz or more), narrow band excimer or molecular fluorine laser system that exhibits high wavelength stability (e.g., less than 0.2 pm, and preferably below 0.1 pm).

It is also an object of the invention to provide the laser system with internal optics that exhibit satisfactory absorption performance in accord with the first object by performing absorption testing prior to insertion of the optics into the laser resonator.

It is a further object of the invention to minimize the time and cost spent on optical components comprising materials that exhibit unsatisfactory absorption performance.

In accord with the above objects, a method is provided for testing a material block prior to forming the material block into one or more optical components for use with a sub-micron lithographic, high power, narrow bandwidth laser system having high wavelength stability (e.g., within 0.1 pm for a sub-picometer bandwidth output beam). The method includes the step of selecting a block of material having appropriate characteristic optical properties such as minimal absorption coefficient or excellent optical homogeneity, at the output emission wavelength(s) of the DUV (e.g., 248 or 193 nm), or VUV (e.g., 157 nm) source laser system being used. For this purpose a material such as fused silica, $MgF_2$ and/or $CaF_2$ (preferred) may be selected for a DUV lithography system, and $CaF_2$ may be selected for use with a VUV system.

The next step of the method of the present invention is to test the material block for absorption performance. Then, if the block exhibits an absorption performance above a predetermined value, then one of more optical components such as one or more prisms, etalons, and/or windows, etc. are formed from the block. Finally, the optical components formed from the block are inserted into the laser resonator to participate in producing a high power, narrow bandwidth laser beam which may be used in sub-micron photolithographic applications. Advantageously, optical components are only formed from material blocks tested as exhibiting sufficient absorption performance, which saves time and cost.

DETAILED DESCRIPTION OF THE PREFERRED EMBODIMENT

Figure 1:
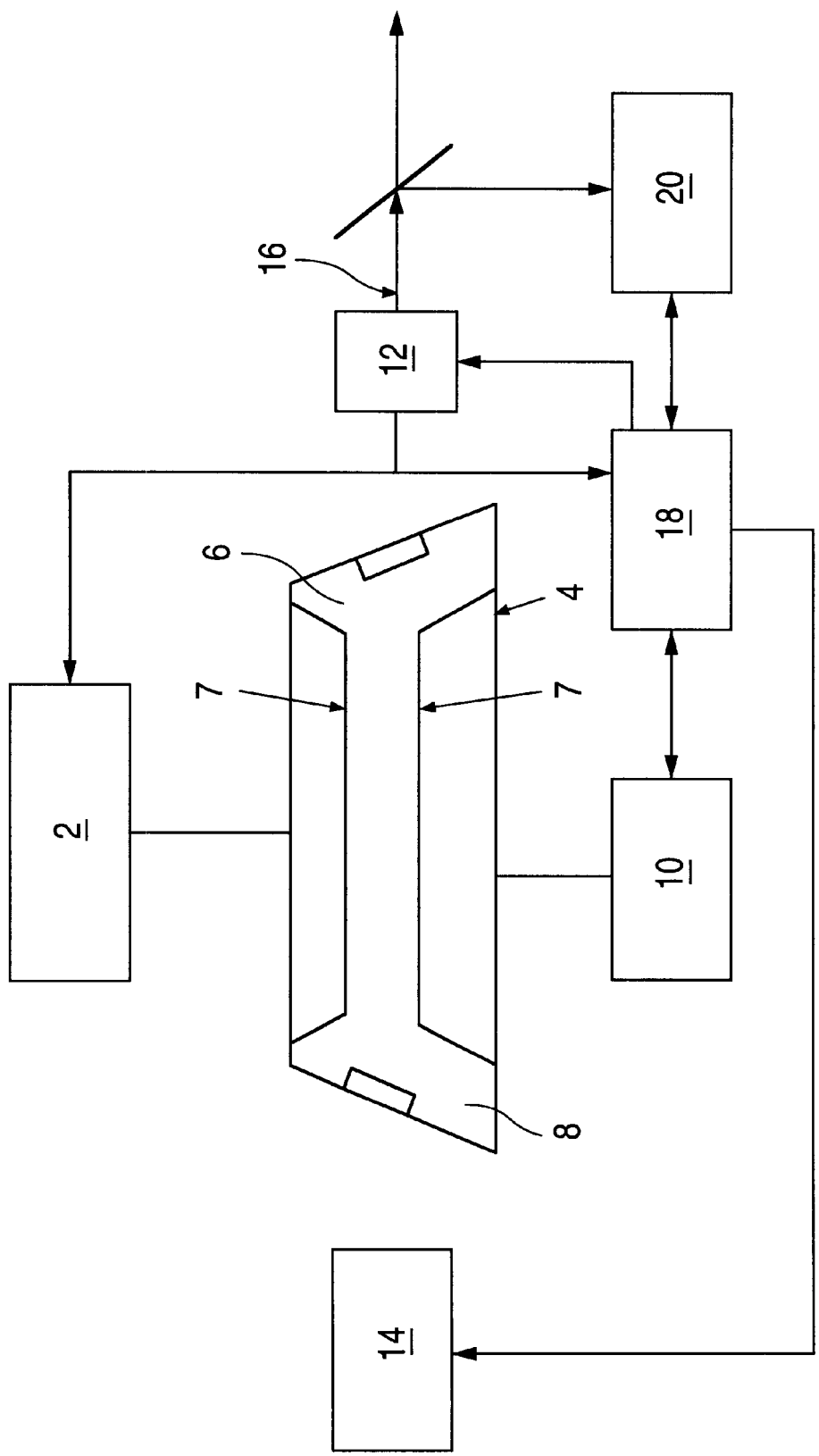
FIG. 1 schematically illustrates a laser system according to a preferred embodiment.
Figure 2:
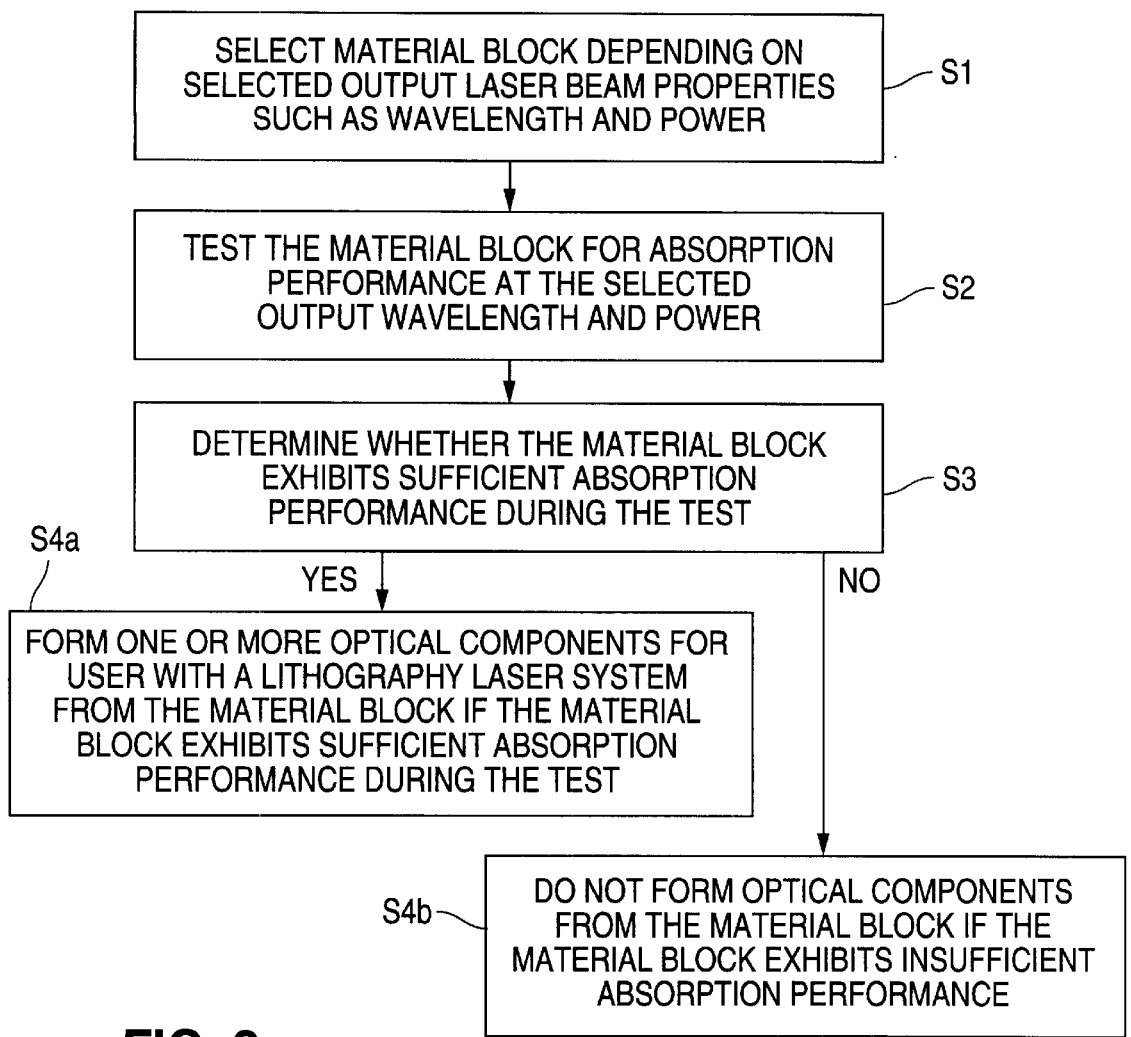
FIG. 2 shows the steps of a preferred optical materials testing method.

The preferred laser system schematically illustrated at FIG. 1 may be an excimer or molecular fluorine laser such as a KrF (248 nm), ArF (193 nm), XeF, XeCl or $F_2$ (157 nm) laser that emits a characteristic output emission spectrum. The laser system includes a discharge circuit 2 and a laser tube 4. The laser tube 4 includes an electrode chamber 6 including a pair of main discharge electrodes 7 and at least one preionization unit (not shown) and a gas flow vessel 8. The discharge circuit 2 provides a high voltage pulse to the main electrodes 7 for energizing a gas mixture between the main electrodes 7.

The gas mixture is circulated from the gas flow vessel 8 through the discharge area in the electrode chamber 6 and preionized by the preionization unit just before the main discharge is applied. A gas supply unit 10 is attached to the laser system for gas replenishment. The discharge area is surrounded by a resonator including a front optics module 12 and rear optics module 14 for generating a laser beam 16. Means for outcoupling the laser beam 16 are also included, preferably within the front optics module 12. Diagnostic components 20 such as an etalon or grating spectrometer and a photodetector for monitoring and controlling the energy of output pulses and the discharge voltage, and/or other beam parameters, as well as the composition of the gas mixture are provided including one or more feedback arrangements using a processor 18. The processor 18 also controls resonator optics of the front and/or rear optics modules 12, 14 for tuning the wavelength of the output beam. The preferred gas control system is described at U.S. patent applications No. 60/124,785, 09/447,882, 60/123,928, 60/171,717 and 09/379,034, each of which is assigned to the same assignee and is hereby incorporated by reference into the present application. Wavelength tuning and line narrowing and/or selection optics are also located within the resonator.

The characteristic output emission spectra of the KrF and ArF lasers is quite broad, i.e., around 500 pm. Line narrowing optics are preferably used for reducing the bandwidth to less than around 20 pm or less depending on requirements of the application. The line narrowing optics may include one or more dispersive prisms, beam expanding optics such as beam expanding prisms or lenses, etalons, gratings, grisms, lenses and/or apertures. The selected line narrowing optics may be such as are described in U.S. Pat. No. 5,761,236 or 5,978,409, or U.S. patent applications No. 09/244,554, 09/629,256, 09/130,277, 60/124,804, 60/124,241 or 60/140, 532, each application of which is assigned to the same assignee as the present invention and is hereby incorporated by reference into the present application.

The molecular fluorine laser characteristically emits two or three closely-spaced lines around 157 nm and has an visible (red) background emission due to atomic fluorine transitions. In this case, preferably one of the VUV lines is selected using line selection optics including one or more of the optical components mentioned above. The line selection optics may be such as are described in any of U.S. Pat. No. 6,154,470 and U.S. patent applications No. 09/317,695, 09/657,396, 60/212,257, 60/173,993 and United States provisional patent application serial no. not yet assigned by Inventors Sergei V.Govorkov and Gongxue Hua, entitled, "Molecular Fluorine Laser with Single Spectral Line and Polarized Output, filed Nov. 16, 2000, each of which is assigned to the same assignee as the present invention and is hereby incorporated by reference into the present application.

A preferred method for testing a block of optical material for determining the absorption performance of the material is shown in the flow diagram at FIG. 1. The method depicted at FIG. 1 is part of a larger picture wherein a laser system is being prepared whose output beam is to be used for an industrial application such as micromachining or microlithography.

Referring to FIG. 1, the first step S1 is selecting a block of material having properties consistent with the output emission parameters of the laser system to be assembled. At DUV wavelengths, materials such as fused silica and $CaF_2$ are preferred (see '236 patent, mentioned above). $MgF_2$ is also adequately transmissive at DUV wavelengths. Quartz, especially crystalline quartz, $BaF_2$, LiF, $SrF_2$, fluorine-doped quartz, and sapphire are other alternative materials. At VUV wavelengths such as 157 nm, $CaF_2$ is preferred, and $MgF_2$ is an alternative.

The second step S2 is to test the block of material to determine whether the absorption performance of the material is sufficient. There are many ways to do this. For example, a laser beam having parameters similar or identical to those of the laser system to be manufactured in accord with the present invention is directed at and at least substantially transmitted through the block. In particular, the wavelength of the laser test radiation should be the same as that of the future laser system. Alternatively, another wavelength may be used and the absorption performance calculated from knowledge of the absorption curve of the material being tested. In either case, the laser would have very nearly constant energy output to increase the reliability of the test.

The absorption of the laser test source by the material of the block may be measured in a number of ways. In a preferred way, two detectors are used. A first detector measures the radiation intensity impinging upon the entrance surface of the optical block that is in the beam path of the laser test beam. A second detector measures the transmitting intensity, i.e., the intensity of radiation exiting the optical block. Alternatively, the laser energy is first measured with the optical test block within the beam path and the laser energy is second measured without the optical test block within the beam path, and both measurements are performed by the same detector. The difference between the two energy or intensity measurements reveals the absorption of the test block.

The detector or detectors used may be photodiode, photomultiplier tube or pyroelectric detectors. The absorption may be determined based on the difference in intensity of the beam before and after traversing the block. Advantageously, this testing of the absorption performance may yield sufficiently measurable results because there is sufficient optical path length in the block to absorb a measurable quantity of the incident laser intensity. Even low absorption coefficients can be determined. In contrast, in the method described by Morton in the '352 patent mentioned above, it would be difficult to measure precisely enough the intensity difference between the beam incident upon and exiting from the prisms described therein, since there is inadequate material comprising each prism being tested.

In a second way, the temperature of the block may be measured at one of more locations along the block. For example, one or more temperature sensors, such as themocouples, may be positioned near the block, on the surface of the block, or implanted into the block for measuring the increase in temperature in a portion or portions of the block as it absorbs test beam radiation and heats up in response.

In a third way, an infrared sensor may be positioned to monitor the temperature of the block as it is heated up by absorption of the test beam by the block. In a fourth way, fluorescence light emanating from the optical block which is emitted by the block during illumination by the DUV or VUV laser radiation test source may be measured. The intensity and/or spectral distribution of (typically visible) fluorescence light can be used as a quality indicator for the block. A high fluorescence intensity would indicate a high absorption coefficient and low quality of the optical material of the block.

In step S3, data gathered during the test measurement procedure performed in step S2 is used to calculate or determine whether the block exhibits sufficient absorption performance. Specifically, if a measured percentage, or percentage calculated from measured data, of the incident source radiation is absorbed by the material of the block below a predetermined percentage, then the block is deemed to exhibit sufficient absorption performance, and the preferred method of the invention proceeds to step S4a. On the other hand, if a percentage of the incident source radiation is absorbed by the material of the block above the predetermined percentage, then the block is deemed to exhibit insufficient absorption performance, and the method proceeds to step S4b.

In step S4a, which is reached after a determination is made in step S3 that the material of the tested block exhibits sufficient absorption performance, one or more or preferably several optical components, such as those described above, are formed from the material. Advantageously, by using the method of the present invention, the manufacture of the optical components can proceed with knowledge that the optical components do exhibit sufficient absorption performance, and the time and cost of manufacture will not be wasted on account of a later determination that the components do not exhibit sufficient absorption performance. The optical components, once formed, can be confidently inserted into the resonator of a laser system.

In step S4b on the other hand, which is reached after a determination is made in step S3 that the material of the tested block does not exhibit sufficient absorption performance, the block of material is either returned to the vendor, or used for another purpose wherein absorption performance standards are somewhat relaxed compared to the present invention. Advantageously, the time and cost of manufacturing optical component(s) from a material block not exhibiting sufficient absorption performance is saved in accord with the present invention.

As discussed above, absorption is a key quality parameter for optical DUV and VUV materials. Another quality parameter is the homogeneity of the index of refraction for DUV and VUV materials used for manufacturing of optical components. The homogeneity is of particular importance for materials for manufacturing beam expanding prisms and intracavity etalon plates that will be used for line-narrowing below 1 pm bandwidth.

The testing for optical homogeneity is performed using a commercial interferometer, and thus differs from the methods for testing absorption described above. However, the idea of the present invention, i.e., to test a block of optical material prior to forming optical components from it to determine whether the quality is high enough, is also applicable to index homogeneity testing. That is, a block of material that is a candidate for forming optical components such as prisms, etalons, windows, etc. for use, e.g., in a line-narrowing module of an excimer or molecular fluorine laser, may be tested for quality using preferably a commercial interferometer prior to forming the components.

Figure 3:
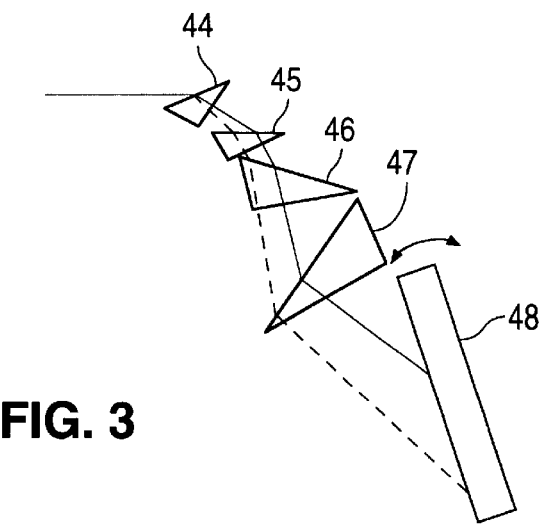
FIG. 3 schematically illustrates a line-narrowing module of a sub 0.6 pm bandwidth laser having a wavelength of 248 nm or less.

FIG. 3 illustrates a line-narrowing and/or selection module for a 193 nm ArF laser in accord with a preferred embodiment. The line-narrowing module shown at FIG. 3 includes a four prism beam expander including four beam expanding prisms 44–47, and a grating 48. The beam expander including prisms 44–47 reduces the divergence and geometrically expands the beam prior to impinging upon the grating which disperses the beam, resulting in a narrowing of the bandwidth or selection of a narrow spectral line. One of ordinary skill in the art would understand that line-narrowing and/or selection may be performed in a number of other ways using dispersion prisms, gratings, grisms, etalons, birefringent plates, etc., such as are described in the patents and patent applications incorporated by reference above, for the 193 nm ArF laser, as well as for the 157 nm $F_2$ laser and 248 nm KrF laser.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the claims that follow, and equivalents thereof.

In addition, in the method claims that follow, the operations have been ordered in selected typographical sequences. However, the sequences have been selected and so ordered for typographical convenience and are not intended to imply any particular order for performing the operations, except for those claims wherein a particular ordering of steps is expressly set forth or understood by one of ordinary skill in the art as being necessary.

What is claimed is:

1. A method for testing a block of material prior to forming one or more optical components from the block for use with a microlithographic, high power, narrow bandwidth laser system having high wavelength stability, comprising the steps of:

selecting a block of material having optical properties adequate for use with a laser system emitting at a wavelength around 248 nm, having a sub 0.6 pm bandwidth and operating at at least 2 kHz;

testing the material block for optical performance;

forming one of more optical components from the block when the results of the testing reveal that the optical performance is satisfactory; and inserting said one or more optical components formed from said block into a wavelength selection module for use within a resonator of a 248 nm or less wavelength, 2000 Hz or higher repetition rate, sub 0.6 pm bandwidth laser configured for use in sub-micron photolithography.

2. The method of claim 1, wherein said testing step includes the step of testing absorption in the block.

3. The method of claim 2, wherein said absorption testing includes measuring the intensity of a laser beam prior to entering the block and after traversing the block, and calculating the difference.

4. The method of claim 2, wherein said absorption testing includes measuring the temperature of the block as a laser beam is incident on the block.

5. The method of claim 4, wherein the temperature is measured using an infrared sensor positioned near the block.

6. The method of claim 4, wherein the temperature is measured using one or more temperature sensors positioned on the block.

7. The method of claim 2, wherein the absorption is tested by measuring the fluorescence intensity from the block as a laser beam is incident on the block.

8. The method of claim 1, wherein said testing step includes the step of testing refractive index homogeneity in the block.

9. The method of claim 8, wherein the refractive index homogeneity is tested by interferometry.

10. The method of claim 1, wherein the optical material is selected from the group of materials consisting of calcium fluoride and magnesium fluoride.

11. The method of claim 10, wherein said wavelength is 193 nm.

12. The method of claim 10, wherein said wavelength is 157 nm.

13. The method of claim 1, wherein the material selected in fused silica.

14. The method of claim 1, wherein the one or more components formed are selected from the group consisting of prisms, etalons, lenses and laser tube windows.

15. The method of claim 1, wherein the one or more components formed are prisms.

16. The method of claim 15, wherein the one or more components are beam expander prisms and the inserting step includes aligning said beam expander prisms for expansion of the beam prior to impinging upon a grating.

17. The method of claim 16, wherein said one or more components are four beam expander prisms and said wavelength is around 193 nm.

* * * * *